(12) United States Patent
Ejlersen

(10) Patent No.: US 8,920,381 B2
(45) Date of Patent: Dec. 30, 2014

(54) INFUSION SET WITH IMPROVED BORE CONFIGURATION

(71) Applicant: Medtronic Minimed, Inc., Northridge, CA (US)

(72) Inventor: Henning Munk Ejlersen, Vedbaek (DK)

(73) Assignee: Medtronic MiniMed, Inc., Northridge, CA (US)

(*) Notice: Subject to any disclaimer, the term of this patent is extended or adjusted under 35 U.S.C. 154(b) by 0 days.

(21) Appl. No.: 13/861,727

(22) Filed: Apr. 12, 2013

(65) Prior Publication Data
US 2014/0309593 A1    Oct. 16, 2014

(51) Int. Cl.
*A61M 5/148*    (2006.01)
*A61M 5/158*    (2006.01)

(52) U.S. Cl.
CPC ....... *A61M 5/158* (2013.01); *A61M 2005/1581* (2013.01)
USPC ........................................... 604/180; 604/174

(58) Field of Classification Search
CPC ............ A61M 5/158; A61M 5/14248; A61M 2005/1581; A61M 2025/0246
USPC .................................. 604/180, 174
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |

(Continued)

FOREIGN PATENT DOCUMENTS

| | | |
|---|---|---|
| DE | 8619002 U1 | 8/1986 |
| DE | 4329229 | 3/1995 |

(Continued)

OTHER PUBLICATIONS

PCT Search Report (PCT/US02/03299), Oct. 31, 2002, Medtronic Minimed, Inc.

(Continued)

*Primary Examiner* — Nicholas Lucchesi
*Assistant Examiner* — Gerald Landry, II
(74) *Attorney, Agent, or Firm* — Ingrassia Fisher & Lorenz, P.C.

(57) ABSTRACT

An infusion set for use with a fluid infusion device is provided. The infusion set can include a mount including a projection having a bore. The projection can be surrounded at least partially by a recess defined through a surface of the mount, and the mount can include at least one rib that spans the recess. The infusion set can include a fluid outlet coupled to at least a portion of the bore of the projection and a coupling device to couple the infusion set to a user. The coupling device can be coupled to the surface and the at least one rib of the mount.

16 Claims, 4 Drawing Sheets

(56) References Cited

U.S. PATENT DOCUMENTS

| | | | |
|---|---|---|---|
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,445,616 A * | 8/1995 | Kratoska et al. ............. 604/141 |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,551,849 A * | 9/1996 | Christiansen ................ 417/472 |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |

(56) References Cited

U.S. PATENT DOCUMENTS

| | | | |
|---|---|---|---|
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,396,330 B2 | 7/2008 | Banet et al. | |
| 7,621,893 B2 | 11/2009 | Moberg et al. | |
| 7,828,764 B2 | 11/2010 | Moberg et al. | |
| 7,905,868 B2 | 3/2011 | Moberg et al. | |
| 2001/0044731 A1 | 11/2001 | Coffman et al. | |
| 2002/0013518 A1 | 1/2002 | West et al. | |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0113761 A1 | 5/2005 | Faust et al. | |
| 2005/0154271 A1 | 7/2005 | Rasdal et al. | |
| 2005/0192557 A1 | 9/2005 | Brauker et al. | |
| 2005/0234405 A1* | 10/2005 | Dikeman et al. | 604/180 |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0000828 A1* | 1/2007 | Norman et al. | 210/198.2 |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2008/0269687 A1 | 10/2008 | Chong et al. | |
| 2008/0281297 A1 | 11/2008 | Pesach et al. | |
| 2009/0081951 A1 | 3/2009 | Erdmann et al. | |
| 2009/0082635 A1 | 3/2009 | Baldus et al. | |
| 2009/0143763 A1* | 6/2009 | Wyss et al. | 604/506 |
| 2009/0221971 A1 | 9/2009 | Mejlhede et al. | |
| 2009/0299290 A1 | 12/2009 | Moberg | |
| 2010/0030156 A1* | 2/2010 | Beebe et al. | 604/182 |
| 2010/0256598 A1* | 10/2010 | Mernoe et al. | 604/506 |
| 2011/0306935 A1* | 12/2011 | Tanaka et al. | 604/174 |
| 2011/0313351 A1* | 12/2011 | Kamen et al. | 604/67 |
| 2012/0209191 A1* | 8/2012 | Gray et al. | 604/134 |
| 2013/0030342 A1* | 1/2013 | Scheremet et al. | 602/48 |
| 2013/0218134 A1* | 8/2013 | Tanaka et al. | 604/540 |
| 2013/0310754 A1* | 11/2013 | Kutsch | 604/180 |

FOREIGN PATENT DOCUMENTS

| | | |
|---|---|---|
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 02/076526 A2 | 10/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting A Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed•Technologies.

(56) References Cited

OTHER PUBLICATIONS (Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.

Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.

(56) References Cited

OTHER PUBLICATIONS

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., at al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, at al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytics Chimica Acta, vol. 218, 1989, pp. 137-142.

\* cited by examiner

INFUSION SET WITH IMPROVED BORE CONFIGURATION

TECHNICAL FIELD

Embodiments of the subject matter described herein relate generally to fluid infusion devices for delivering a medication fluid to the body of a user. More particularly, embodiments of the subject matter relate to systems for an insulin infusion set having an improved bore configuration for use with a fluid infusion device.

BACKGROUND

Certain diseases or conditions may be treated, according to modern medical techniques, by delivering a medication or other substance to the body of a user, either in a continuous manner or at particular times or time intervals within an overall time period. For example, diabetes is commonly treated by delivering defined amounts of insulin to the user at appropriate times. Some common modes of providing insulin therapy to a user include delivery of insulin through manually operated syringes and insulin pens. Other modern systems employ programmable fluid infusion devices (e.g., insulin pumps) to deliver controlled amounts of insulin to a user.

A fluid infusion device suitable for use as an insulin pump may be realized as an external device or an implantable device, which is surgically implanted into the body of the user. External fluid infusion devices include devices designed for use in a generally stationary location (for example, in a hospital or clinic), and devices configured for ambulatory or portable use (to be carried by a user). External fluid infusion devices may establish a fluid flow path from a fluid reservoir to the user via, for example, a hollow tubing. The hollow tubing may be connected to a hollow fluid delivery needle that is designed to pierce the user's skin to deliver an infusion medium to the body. Alternatively, the hollow tubing may be connected directly to the user's body through a cannula or set of micro-needles. In order to ensure proper fluid delivery, the hollow tubing needs to be properly coupled to the user's body.

Accordingly, it is desirable to provide an infusion set having an improved bore configuration for coupling of a hollow tubing in communication with a fluid infusion device to a user's body to ensure proper insulin delivery. Furthermore, other desirable features and characteristics will become apparent from the subsequent detailed description and the appended claims, taken in conjunction with the accompanying drawings and the foregoing technical field and background.

BRIEF SUMMARY

According to various exemplary embodiments, an infusion set for use with a fluid infusion device is provided. The infusion set can comprise a mount including a projection having a bore. The projection can be surrounded at least partially by a recess defined through a surface of the mount, and the mount can include at least one rib that spans the recess. The infusion set can include a fluid outlet coupled to at least a portion of the bore of the projection and a coupling device to couple the infusion set to a user. The coupling device can be coupled to the surface and the at least one rib of the mount.

Also provided according to various embodiments is an infusion set for use with a fluid infusion device. The infusion set can include a connector to fluidly couple the fluid infusion device to the infusion set. The infusion set can also include a mount having a distal end coupled to the connector and a proximal end. The mount can include a projection having a bore that extends along an axis. The proximal end can include a plurality of ribs that extend from a surface of the proximal end to the projection. The plurality of ribs can be arranged to lie in a plane transverse to the axis. The infusion set can include a fluid outlet coupled to at least a portion of the bore of the mount to be in fluid communication with the fluid infusion device through the connector. The infusion set can also comprise a coupling device to couple the infusion set to a user. The coupling device can be coupled to the surface and each of the plurality of spaced apart ribs of the proximal end.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

The following description relates to a fluid infusion device of the type used to treat a medical condition of a user. The infusion device can be used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: U.S. Patent Publication Nos. 2009/0299290 and 2008/0269687; U.S. Pat. Nos. 4,562,751; 4,678,408; 4,685,903; 5,080,653; 5,505,709; 5,097,122; 6,485,465; 6,554,798; 6,558,351; 6,659,980; 6,752,787; 6,817,990; 6,932,584; 7,621,893; 7,828,764; and 7,905,868; which are each incorporated by reference herein.

Figure 1:
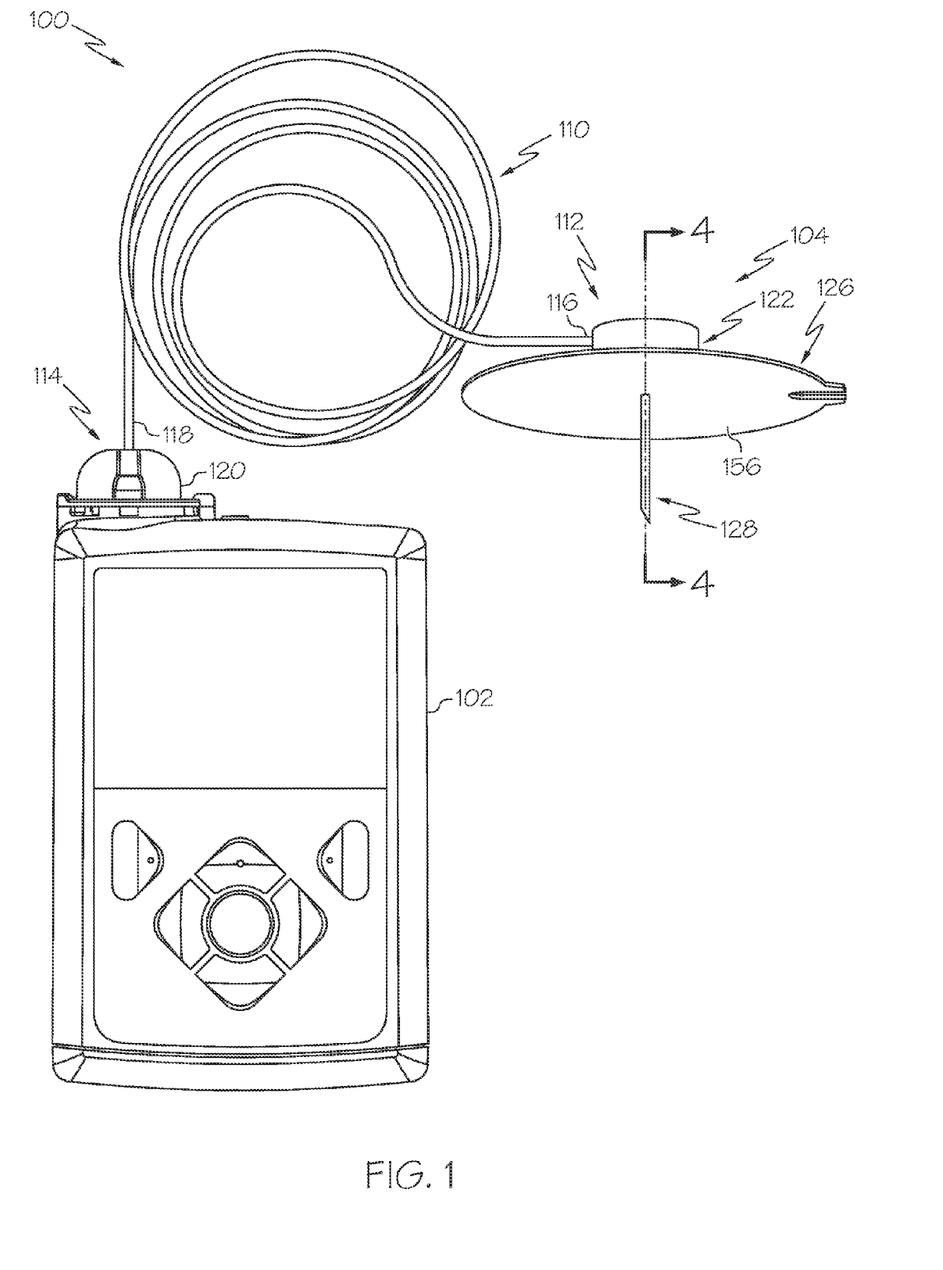
FIG. 1 is a perspective view of an exemplary embodiment of a fluid infusion device including an infusion set according to various teachings of the present disclosure.

FIG. 1 is a perspective view of an exemplary embodiment of a fluid infusion system 100. The fluid infusion system 100 includes two main components: a fluid infusion device 102 (e.g., an insulin pump) and an infusion set component 104, which can be coupled to the fluid infusion device 102 as depicted in FIG. 1. The infusion set component 104 can include, without limitation: a tube 110, an infusion unit 112 and a connector assembly 114. The infusion unit 112 can be coupled to a first end 116 of the tube 110 and the connector assembly 114 can be coupled to a second end 118 of the tube 110. The fluid infusion device 102 can be carried or worn by the user, and the infusion set component 104 terminates at the infusion unit 112 such that the fluid infusion device 102 can deliver fluid to the body of the user via the tube 110. Thus, the infusion unit 112 can be coupled to the body of the user, as described in more detail below. The fluid infusion device 102 may leverage a number of conventional features, components, elements, and characteristics of existing fluid infusion devices. For example, the fluid infusion device 102 may incorporate some of the features, components, elements, and/ or characteristics described in U.S. Pat. Nos. 6,485,465 and 7,621,893, the relevant content of which is incorporated by reference herein. It should be noted that the fluid infusion device 102 illustrated herein is merely exemplary, as any suitable fluid infusion device can be employed with the infusion set component 104. Furthermore, the techniques described herein for coupling the infusion unit 112 to the body of a user can be employed with other devices, such as an analyte monitoring device coupled to the body of a user. Thus, the following description is merely exemplary and is not intended to limit the scope of the appended claims.

The fluid infusion device 102 accommodates a fluid reservoir (hidden from view in FIG. 1) for the fluid to be delivered to the user. The tube 110 represents the fluid flow path that couples the fluid reservoir to the infusion unit 112. When installed as depicted in FIG. 1, the tube 110 extends from the fluid infusion device 102 to the infusion unit 112, which in turn provides a fluid pathway to the body of the user. For the illustrated embodiment, the connector assembly 114 is realized as a removable reservoir cap 120 (or fitting) that is suitably sized and configured to accommodate replacement of fluid reservoirs (which are typically disposable) as needed.

In this regard, the reservoir cap 120 is designed to accommodate the fluid path from the fluid reservoir to the tube 110.

Figure 2:
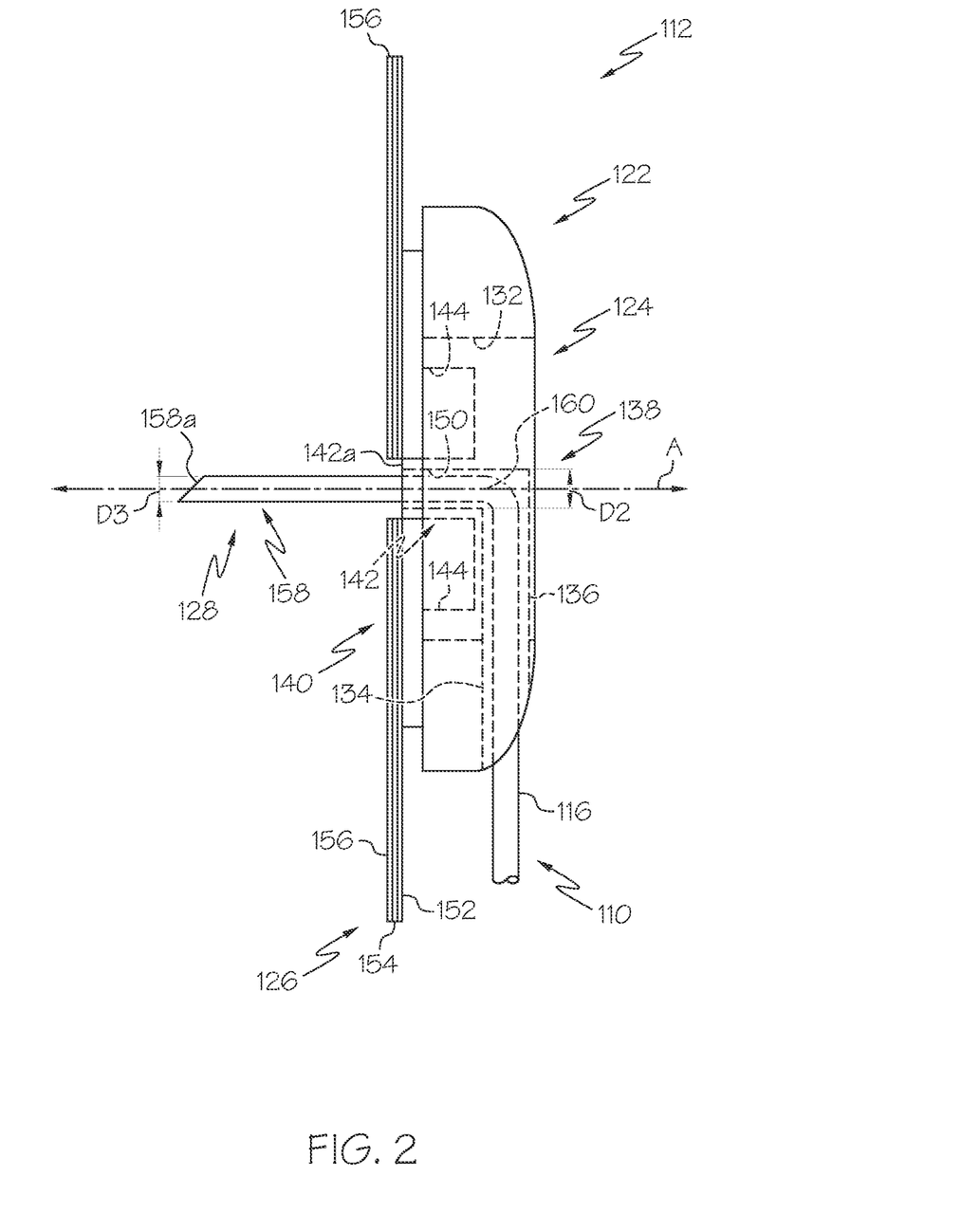
FIG. 2 is a side view of the exemplary infusion set of FIG. 1.

With reference to FIG. 2, a schematic side view of the infusion unit 112 is shown. In one example, the infusion unit 112 can include a connector 122, a mount 124, a coupling device 126 and a fluid outlet 128. The connector 122 can be coupled to the first end 116 of the tube 110 and to the mount 124. The connector 122 can have any desired shape and configuration to facilitate fluid flow from the tube 110 through the infusion unit 112. In one example, the connector 122 can be substantially annular and can define a throughbore 132 for coupling the connector 122 to the mount 124. The connector 122 can also define a passageway 134, which can enable the first end 116 of the tube 110 to pass through the connector 122. The tube 110 can be coupled to the connector 122 through any suitable technique, including, but not limited to, press-fit, adhesives, etc. The passageway 134 can be in communication with a passageway 136 of the mount 124 to enable the tube 110 to be fluidly coupled to the fluid outlet 128.

With continued reference to FIG. 2, the mount 124 can include a first or distal end 138, a second or proximal end 140, the passageway 136, an internal projection 142 and an internal recess 144. In one example, the connector 122 can be coupled to the distal end 138 and the coupling device 126 can be coupled to the proximal end 140. Generally, the distal end 138 can be sized so as to be received within the throughbore 132 of the connector 122. The distal end 138 of the mount 124 can be coupled to the connector 122 via any suitable technique, including, but not limited to, a press-fit, snap-fit, etc. The distal end 138 can have any desired shape that can cooperate with the connector 122, and in one example, can be substantially cylindrical.

The proximal end 140 can be coupled to the distal end 138. The proximal end 140 can be substantially annular, and can have a diameter, which can be greater than a diameter of the distal end 138. The proximal end 140 can have a height along an axis A of the infusion unit 112, which can be less than a height of the distal end 138 defined along the axis A. In one example, with reference to FIG. 3, the proximal end 140 can have at least one or a plurality of ribs 146. For example, the proximal end 140 can include about eight ribs. The ribs 146 can span the internal recess 144, to couple or connect the internal projection 142 with a surface 148 of the proximal end 140. In one example, the ribs 146 can be arranged at substantially evenly spaced intervals about a perimeter or circumference of the internal projection 142, however, the ribs 146 could be arranged so as to be spaced at different intervals or distances from each other about the perimeter of the internal projection 142. The ribs 146 can provide structural support to the internal projection 142, which can aid in maintaining the position of the fluid outlet 128 in the body of the user. In this regard, the ribs 146 can stiffen the internal projection 142, which can receive the fluid outlet 128 therethrough, and thereby the ribs 146 can aid in ensuring the fluid outlet 128 remains positioned along the axis A even with relative movement between the infusion unit 112 and the body of the user.

Figure 3:
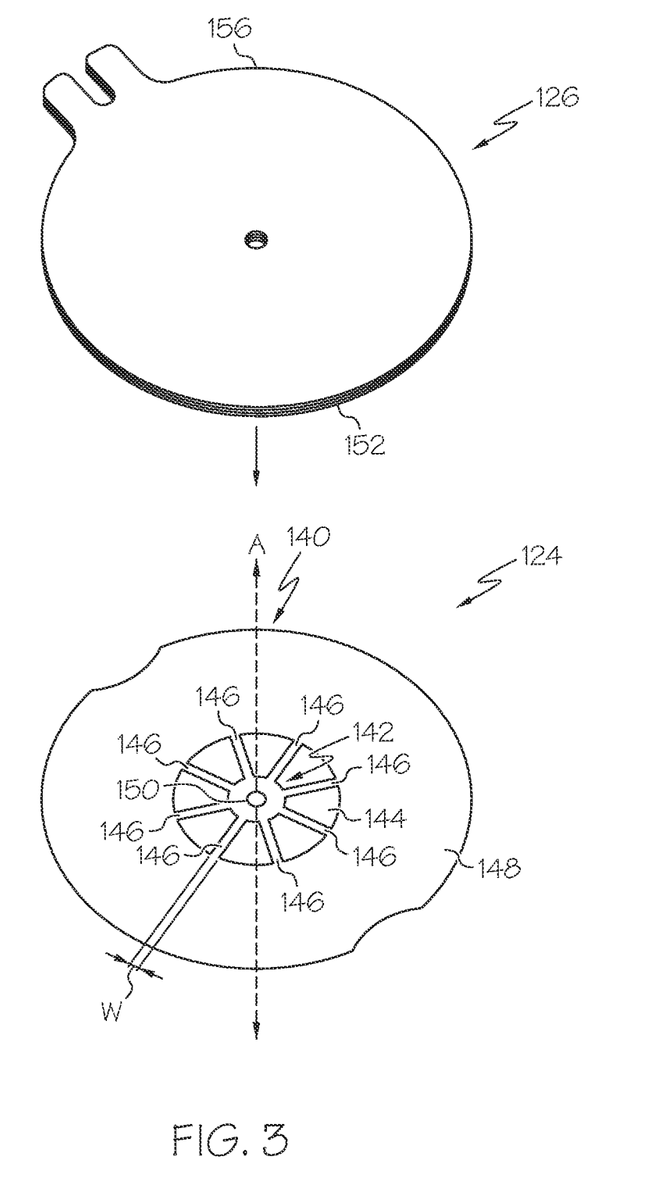
FIG. 3 is a partially exploded view of the exemplary infusion set of FIG. 1.

In one example, the ribs 146 can be substantially rectangular, however, the ribs 146 can have any desired shape. The ribs 146 can generally lie in a plane that is transverse to the axis A of the infusion unit 112, and can be substantially symmetric with respect to the axis A. In one example, the ribs 146 can extend radially from the axis A. The ribs 146 can have a width W that can be sized to enable a portion of the coupling device 126 to be coupled to the mount 124 so that the coupling device 126 is positioned adjacent to the internal projection 142. Generally, it is desirable to position the coupling device 126 as close to the internal projection 142 as possible to assist in maintaining the location of the fluid outlet 128 in the body of the user. It should be noted that the ribs 146 as described and illustrated herein are merely exemplary, and the proximal end 140 could have any number of ribs 146 in any desired shape to facilitate positioning a portion of the coupling device 126 adjacent to the internal projection 142. Furthermore, the proximal end 140 could include a wall that extends from the surface 148 to the internal projection 142 such that the internal recess 144 is substantially completely enclosed.

With reference to FIG. 2, the passageway 136 of the mount 124 can be in communication with a bore 150 defined through at least a portion of the internal projection 142. The bore 150 can be sized to receive at least a portion of the fluid outlet 128 to couple the fluid outlet 128 to the mount 124. In one example, the bore 150 can have a diameter D2 that can be substantially the same as a diameter D3 of the fluid outlet 128. For example, the diameter D2 of the bore 150 can be about 0.8 millimeters (mm) and the diameter D3 of the fluid outlet 128 can be substantially about 0.8 mm.

The internal projection 142 can be substantially cylindrical, and can extend from the distal end 138 to the proximal end 140. The internal projection 142 can generally extend through the internal recess 144 along the axis A of the infusion unit 112. The internal projection 142 can support and impart rigidity to the fluid outlet 128, and the ribs 146 can support and impart rigidity to the internal projection 142. The internal projection 142 can have a sidewall with a thickness selected such that the ribs 146 are substantially adjacent to the fluid outlet 128. By placing the ribs 146 closer to the fluid outlet 128, the coupling device 126 can be coupled closer to the fluid outlet 128, which can assist in maintaining the location of the fluid outlet 128 relative to the user during movement of the user.

The internal recess 144 can be defined through the surface 148 of the proximal end 140 and can extend through the proximal end 140 and a portion of the distal end 138. The internal recess 144 can provide the infusion unit 112 with flexibility such that the infusion unit 112 can move with the body of the user. The internal recess 144 can be substantially annular. It should be noted that the use of the internal recess 144 is merely exemplary, as the infusion unit 112 need not include the internal recess 144, if desired.

The coupling device 126 can couple the mount 124 to the body of the user. In one example, the coupling device 126 can comprise a mounting layer 152, an adhesive layer 154 and a backing 156. It should be noted that the mounting layer 152 and backing 156 are illustrated herein as having a nominal thickness, but that the mounting layer 152 and backing 156 could have any suitable thickness as necessary for the manufacture of the coupling device 126. The mounting layer 152 and adhesive layer 154 can be separately or integrally formed. The mounting layer 152 can couple or fixedly attach the adhesive layer 154 to the mount 124. The mounting layer 152 can be coupled or secured to the proximal end 140 of the mount 124 through any suitable technique, including, but not limited to, ultrasonic welding. Generally, the mounting layer 152 can be coupled to substantially all surface areas of the proximal end 140 of the mount 124. Thus, the mounting layer 152 can be coupled to the ribs 146 and the surface 148 of the proximal end 140. It should be noted that an end 142a of the internal projection 142 may not be coupled to the coupling device 126, if desired. In addition, while the mounting layer 152 is illustrated herein as being defined over substantially an entire surface of the coupling device 126, the mounting layer 152 can be coupled to just a portion of the surface of the adhesive layer 154. For example, the mounting layer 152 can be coupled to the adhesive layer 154 so as to extend over a portion of the adhesive layer 154 that corresponds with the portion of the coupling device 126 that is coupled to the mount 124. In other words, the mounting layer 152 can be sized to correspond to the size of the mount 124, and can have a radius that can be substantially smaller than a radius of the adhesive layer 154.

The adhesive layer 154 can enable the mount 124 to be removably coupled to the body of the user. It should be noted that the use of the adhesive layer 154 is merely exemplary, as any suitable technique could be used to removably couple the mount 124 to the user. The backing 156 can be coupled to at least a portion of the adhesive layer 154, and can be removed to facilitate coupling the coupling device 126 to the user, as is generally known in the art.

The fluid outlet 128 can be coupled to the tube 110, and can extend through the bore 150 of the internal projection 142. In one example, the fluid outlet 128 can comprise a portion of the first end 116 of the tube 110, however, the fluid outlet 128 can comprise a separate fluid conduit coupled to the first end 116 of the tube 110, including, but not limited to, a hollow needle, cannula, etc. Generally, the fluid outlet 128 can be composed of a suitable biocompatible material, such as a biocompatible polymer, however, the fluid outlet 128 can be composed of a suitable biocompatible metal or metal alloy, if desired. In the case of the fluid outlet 128 being composed of a biocompatible polymer, the ribs 146 and diameter D2 of the internal projection 142 can impart rigidity to the polymeric fluid outlet 128. At least a portion of the fluid outlet 128 can be received into a portion of the body of the user, to enable the fluid from the fluid infusion device 102 to flow into the body of the user. For example, with reference to FIG. 4, a first or proximal end 158 of the fluid outlet 128 can be received into a body B of the user, and a second or distal end 160 can be coupled to the first end 116 of the tube 110. The proximal end 158 can include a piercing tip 158a, however, the proximal end 158 can be atraumatic. In one example, the fluid outlet 128 can be substantially cylindrical, and can have the diameter D3, which can be substantially about equal to the diameter D2 of the bore 150. The fluid outlet 128 can be coupled to the mount 124 through any suitable technique, including, but not limited to, press-fitting, adhesives, etc.

Figure 4:
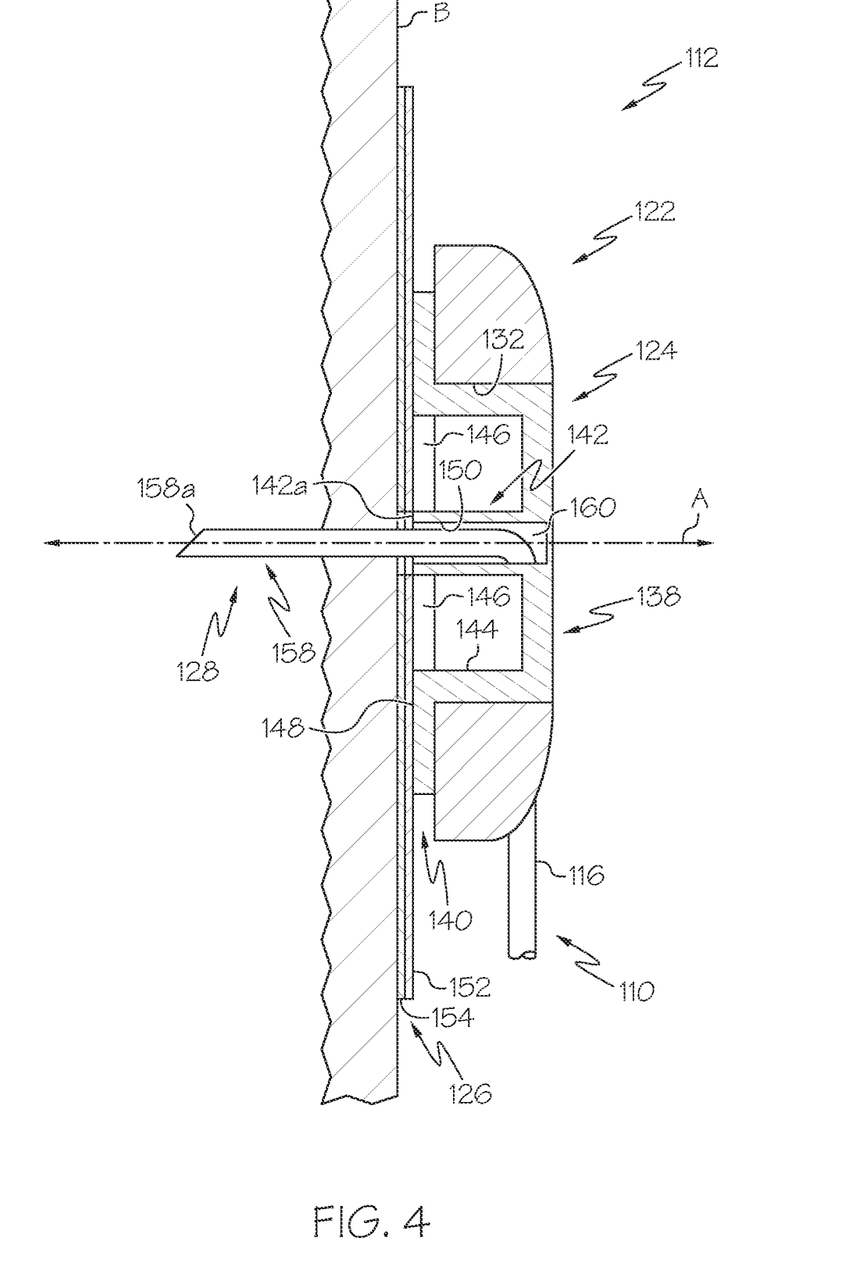
FIG. 4 is an environmental cross-sectional view of the exemplary infusion set of FIG. 1, taken along line 4-4 of FIG. 1.

In order to assemble the infusion unit 112, with reference to FIGS. 2 and 4, the coupling device 126 can be coupled to the mount 124. Then, the tube 110 can be coupled to the fluid outlet 128, and then coupled to or inserted through the passageway 134 of the connector 122, passageway 136 of the mount 124 and the bore 150. In one example, with the tube 110 in communication with the infusion unit 112, the tube 110 can be coupled to the fluid infusion device 102. Then, the infusion unit 112 can be coupled to the body B of the user (FIG. 4). For example, the backing 156 of the coupling device 126 can be removed to expose the adhesive 152 (FIG. 2). Then, the infusion unit 112 can be coupled or pressed onto the body B of the user, so that at least a portion of the fluid outlet 128 extends into the body B of the user, and the mount is removably coupled to the user via the coupling device 126 (FIG. 4). With the infusion unit 112 coupled to the user, fluid from the fluid reservoir of the fluid infusion device 102 can flow through the infusion unit 112 into the body B of the user.

In addition, by providing the bore 150 with the diameter D2 about substantially the same as the diameter D3 of the fluid outlet 128, the internal projection 142 can impart stability and reinforcement to the fluid outlet 128. This can ensure that the fluid outlet 128 remains disposed substantially along the axis A of the infusion unit 112 during movement of the user relative to the infusion unit 112, such as when the user is sleeping, for example. Further, by coupling the coupling device 126 to the ribs 146, which are adjacent to the bore 150, the infusion unit 112 is further secured to the user to ensure that the fluid outlet 128 remains disposed substantially along the axis A of the infusion unit 112 during movement of the user relative to the infusion unit 112.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An infusion set for use with a fluid infusion device, comprising:
   a mount having a first end opposite a second end, the mount including an internal projection having a bore, the internal projection extending from the first end to the second end within the mount, the internal projection surrounded at least partially by an internal recess defined through a surface of the second end of the mount, the second end of the mount including at least one rib that spans the internal recess;
   a fluid outlet coupled to at least a portion of the bore of the internal projection; and
   a coupling device to couple the infusion set to a user, the coupling device coupled to the surface and the at least one rib of the second end of the mount.

2. The infusion set of claim 1, further comprising:
   a connector to fluidly couple the fluid infusion device to the infusion set,
   wherein the connector is coupled to the first end of the mount to fluidly couple the fluid outlet with the fluid infusion device.

3. The infusion set of claim 1, wherein the at least one rib further comprises a plurality of ribs.

4. The infusion set of claim 3, wherein the internal projection is substantially annular and the plurality of ribs are substantially evenly spaced about a perimeter of the internal projection.

5. The infusion set of claim 3, wherein the coupling device is solely coupled to the surface and the plurality of ribs.

6. The infusion set of claim 5, wherein the coupling device further comprises an adhesive.

7. The infusion set of claim 1, wherein the bore has a first diameter that is about equal to a second diameter of the fluid outlet.

8. The infusion set of claim 1, wherein the infusion set is an insulin infusion set for use with an insulin infusion device.

9. An infusion set for use with a fluid infusion device, comprising:
   a connector to fluidly couple the fluid infusion device to the infusion set;
   a mount having a distal end coupled to the connector and a proximal end, the mount including an internal projection defined within the mount from the distal end to the proximal end, the internal projection including a first end opposite a second end and having a bore that extends along an axis, the first end of the internal projection defined at the distal end and the second end of the internal projection defined at the proximal end of the mount, the proximal end including a plurality of ribs that extend from a surface of the proximal end to the second end of the internal projection, the plurality of ribs arranged to lie in a plane transverse to the axis;
   a fluid outlet coupled to at least a portion of the bore of the mount to be in fluid communication with the fluid infusion device through the connector; and
   a coupling device to couple the infusion set to a user, the coupling device coupled to the surface and each of the plurality of spaced apart ribs of the proximal end.

10. The infusion set of claim 9, wherein the internal projection is surrounded at least partially by a recess defined through the surface of the proximal end, and each of the plurality of ribs span the recess.

11. The infusion set of claim 10, wherein the plurality of ribs are substantially evenly spaced about a perimeter of the second end of the internal projection.

12. The infusion set of claim 11, wherein the plurality of ribs are symmetric with respect to the axis.

13. The infusion set of claim 10, wherein the internal projection is substantially annular and the plurality of ribs are substantially evenly spaced about a perimeter of the internal projection.

14. The infusion set of claim 9, wherein the coupling device is solely coupled to the surface and the plurality of ribs.

15. The infusion set of claim 14, wherein the coupling device further comprises an adhesive.

16. The infusion set of claim 9, wherein the bore has a first diameter of about 0.8 millimeters.

* * * * *